United States Patent
Yang et al.

(10) Patent No.: US 12,344,950 B2
(45) Date of Patent: Jul. 1, 2025

(54) SUGAR FORMATION FROM $CO_2$ ELECTROREDUCTION

(71) Applicant: The Regents of the University of California, Oakland, CA (US)

(72) Inventors: Peidong Yang, Berkeley, CA (US); Stefano Cestellos-Blanco, Berkeley, CA (US); Yifan Li, Berkeley, CA (US); Michael B. Ross, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 119 days.

(21) Appl. No.: 18/458,190

(22) Filed: Aug. 30, 2023

(65) Prior Publication Data

US 2023/0407491 A1     Dec. 21, 2023

Related U.S. Application Data

(63) Continuation of application No. PCT/US2022/019183, filed on Mar. 7, 2022.

(60) Provisional application No. 63/158,337, filed on Mar. 8, 2021.

(51) Int. Cl.
  *C25B 3/26*     (2021.01)
  *C07H 3/02*     (2006.01)
  *C25B 3/07*     (2021.01)
  *C25B 11/061*   (2021.01)

(52) U.S. Cl.
  CPC ............. *C25B 3/26* (2021.01); *C07H 3/02* (2013.01); *C25B 3/07* (2021.01); *C25B 11/061* (2021.01)

(58) Field of Classification Search
  None
  See application file for complete search history.

(56) References Cited

U.S. PATENT DOCUMENTS

2022/0042198 A1*  2/2022  Palmore .................... C25F 3/26

OTHER PUBLICATIONS

Socha et al. (React. Kinet. Catal. Lett., vol. 14, No. 2, 119-128 '1980') (Year: 1980).*
Ross et al. (Nature Catalysis | vol. 2 | Aug. 2019 | 648-658) (Year: 2019).*
International Search Report for priority PCT/US22/19183, 11 pages (Jun. 14, 2022).
Mizuno et al., "Synthesis and Utilization of Formose Sugars", Advances in Carbohydrate Chemistry and Biochemistry, vol. 29 (1974), p. 173-227.
Kim et al, "Copper nanoparticle ensembles for selective electroreduction of CO2 to C2-C3 products", Proceedings of the National Academy of Sciences of the United States of America, vol. 114, issue 40, Oct. 3, 2017 (Oct. 3, 2017), p. 10560-10565.

* cited by examiner

*Primary Examiner* — Wojciech Haske
(74) *Attorney, Agent, or Firm* — Richard Aron Osman

(57) ABSTRACT

Formaldehyde is obtained from $CO_2$ through hydrogenation of $CO_2$ to methanol while the subsequent oxidation of methanol yields formaldehyde. This formaldehyde combined with the electrochemically produced glycolaldehyde generates sugars, thus establishing a route from $CO_2$ to sugars.

5 Claims, 6 Drawing Sheets

SUGAR FORMATION FROM $CO_2$ ELECTROREDUCTION

INTRODUCTION

The formose reaction is a one-pot synthesis that yields varied $C_{3-6}$ sugars including glucose.[1] Historically, researchers have combined formaldehyde with an alkaline earth metal catalyst under slight heating conditions to obtain this soup of sugars.[2] The reaction has been thought to proceed through a slow isomerization of formaldehyde to glycolaldehyde.[3] However, more recent studies have confirmed that pre-formed glycolaldehyde is a key autocatalyst for the formose reaction.[4] In fact, glycolaldehyde alone undergoes conversion to sugars. Notably, the formose reaction does not readily take place in an aqueous solution without a source of glycolaldehyde.[4,5] Previous studies on the formose reaction listing formaldehyde as the sole carbon reactant likely contained trace impurities of glycolaldehyde.[4] Formaldehyde could be obtained from $CO_2$ through industrially-established high temperature and pressure hydrogenation of $CO_2$ to methanol and subsequent formox process to yield formaldehyde from methanol.[6] However, there is no clear path for converting $CO_2$ to glycolaldehyde, which is traditionally obtained through biomass pyrolysis.[7] Direct production of glycolaldehyde from $CO_2$ is needed for the realization of formose reaction based sugar generation.

Here we disclose an overall method to convert $CO_2$ to sugars. Formaldehyde is obtained from $CO_2$ through hydrogenation of $CO_2$ to methanol while the subsequent oxidation of methanol yields formaldehyde. This formaldehyde combined with the electrochemically produced glycolaldehyde generates sugars, thus establishing a route from $CO_2$ to sugars. No one has previously shown how electrochemically produced glycolaldehyde from $CO_2$ can be used to catalyze the conversion of formaldehyde to sugars.

SUMMARY OF THE INVENTION

The invention provides a viable approach for the conversion of $CO_2$ to sugar carbohydrates, wherein glycolaldehyde obtained from the electrochemical reduction of $CO_2$, preferably using copper nanocatalysts, is used as an autocatalyst in a formose reaction, yielding a range of C3 to C8 carbohydrates. $CO_2$ is an abundant resource and its electrochemical reduction can be powered using renewable energy sources. These building blocks can be both easy to access and often cheap to acquire. Both key components for this reaction are also readily available in extraterrestrial settings such as Mars, making it an attractive mean to sustain sugars generation during deep space missions In an aspect the invention provides a method making a sugar, comprising: electrochemically reducing $CO_2$ to form glycolaldehyde, wherein the glycolaldehyde then operates as an autocatalyst to promote conversion of formaldehyde to the sugar in a formose reaction.

In embodiments:
the method further comprising: generating the formaldehyde from $CO_2$ through hydrogenation of $CO_2$ to methanol, and oxidizing the methanol yields formaldehyde;
the electrochemical reduction employs a copper nanoparticle based electrocatalyst as a cathode in an electrochemical $CO_2$ reduction environment;
the electrochemical reduction employs a Pt mesh as an anode to balance charge by the oxygen evolution reaction;
the electrochemical reduction employs an electrochemical $CO_2$ reduction environment provided by $KHCO_3$ saturated with constantly flowing pure $CO_2$;
the sugar is selected from tetroses, pentoses, hexoses, heptoses and octoses;
the method is powered by solar energy;
the method is performed in an extraterrestrial environment;
the method further comprising isolating the resultant sugar; and/or
the method further comprising formulating the resultant sugar in a feedstock configured for *E. coli* bacteria.

The invention encompasses all combinations of the particular embodiments recited herein, as if each combination had been laboriously recited.

BRIEF DESCRIPTION OF THE DRAWINGS

FIGS. 6A-C. Utilization of $CO_2$ Sugar as a bacterial feedstock. (a) Optical density measurements of *Escherichia* coli (*E. coli*) cultured with formose sugars (blue) and $CO_2$ Sugars (red). Control is $CO_2$ Sugars without *E. coli* (green). (b) Picture comparing the visual differences between *E. coli* cultures provided with different sugars. From left to right: I. glucose, II. formose sugars, III. $CO_2$ Sugars, and IV. $CO_2$ Sugars without *E. coli*. (c) $^1$H-NMR spectra of $CO_2$ Sugar containing minimal medium pre- and post-*E. coli* culture growth. Inset shows magnified 1-4 ppm region.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polypeptide sequences are understood to encompass opposite strands as well as alternative backbones described herein. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Figure 1:
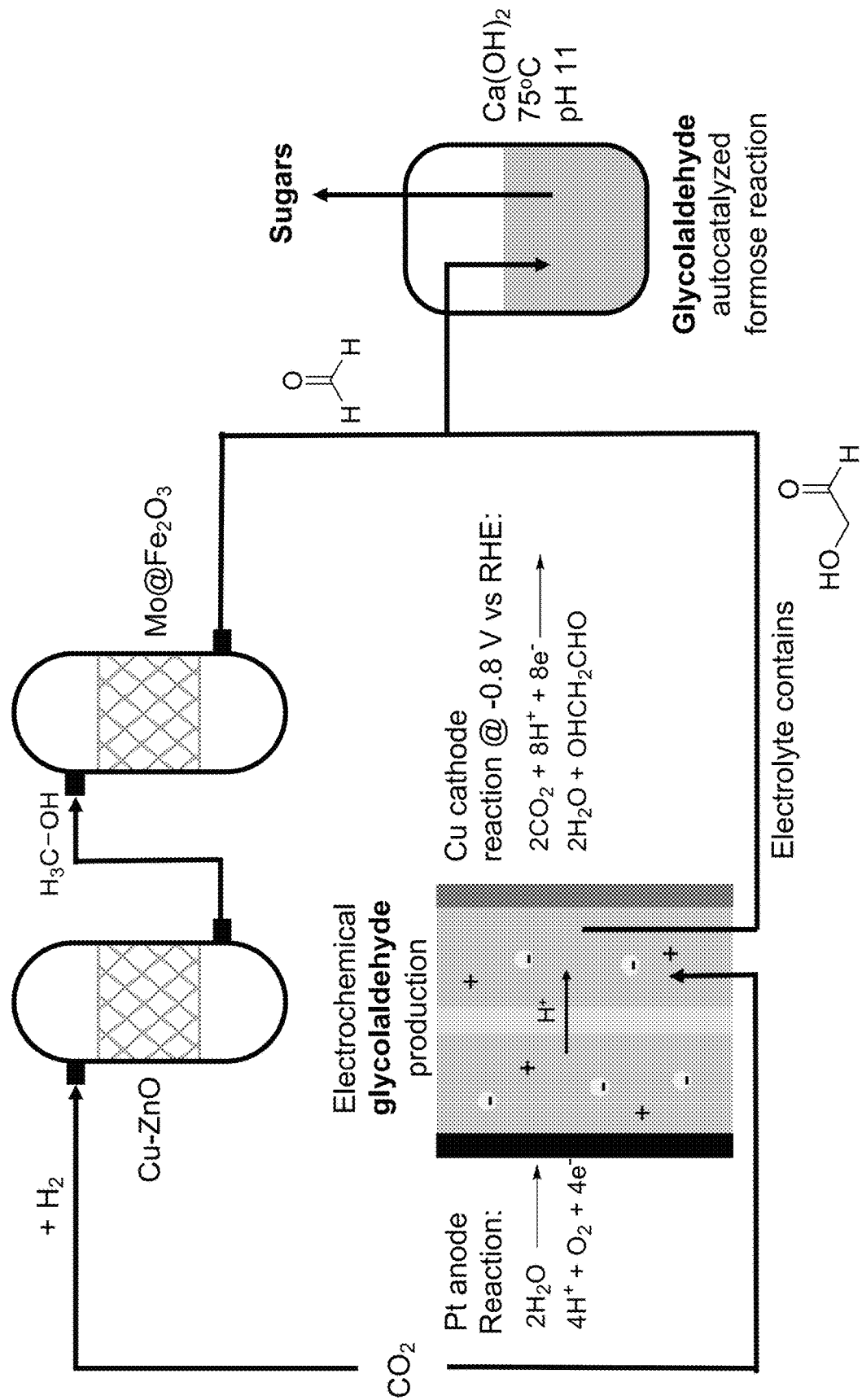
FIG. 1. Generation of sugars from $CO_2$ and $H_2$. Our process flow combines glycolaldehyde from $CO_2$ electrolysis, a key autocatalyst for the formose reaction, with formaldehyde obtained by $CO_2$ hydrogenation and subsequent formox process.

We demonstrate that glycolaldehyde obtained from electrochemical reduction of $CO_2$ serves as the requisite autocatalyst for formose-based sugar generation in the presence of formaldehyde, providing an abiotic pathway from $CO_2$ to sugars. Formaldehyde can be produced from $CO_2$ thus realizing a direct route for inorganic $CO_2$-to-sugar conversion (FIG. 1). By example we have produced glycolaldehyde ($C_2H_4O_2$) directly from electro-reduced $CO_2$ using a copper nanoparticle catalyst. This glycolaldehyde acts as an essential autocatalyst to enable the conversion of formaldehyde to sugars, including tetroses, pentoses, hexoses, heptoses and octoses. Without glycolaldehyde the reaction yields solely methanol and formate.

Electrocatalysis offers a flexible platform, powerable by solar energy for the conversion of $CO_2$ to higher value carbon-based chemicals.[8] However, electrochemical $CO_2$-to-sugar conversion has not been established or theorized. Therefore, we have focused our attention on the 8-electron electrocatalytic conversion of $CO_2$ to glycolaldehyde, the aforementioned key autocatalyst for the formose reaction. Notably, glycolaldehyde can be considered a "$C_2$ carbohydrate" given its molecular formula of $C_2$ $(H_2O)_2$. For this reaction, we have developed a copper nanoparticle based electrocatalyst as the cathode in an electrochemical $CO_2$ reduction environment (e.g. 0.1 M $KHCO_3$ saturated with constantly flowing pure $CO_2$). We used a Pt mesh as the anode to balance charge by the oxygen evolution reaction—however, substitute oxygen evolution reaction (OER) catalysts may be used here to improve energy efficiency or cost. The cathode converts $CO_2$ to multi-electron, multi-carbon products including glycolaldehyde. This cathode is adapted from our previous work on copper-based catalysts for efficient conversion of $CO_2$ to multi-carbons.[9]

Figure 2A:
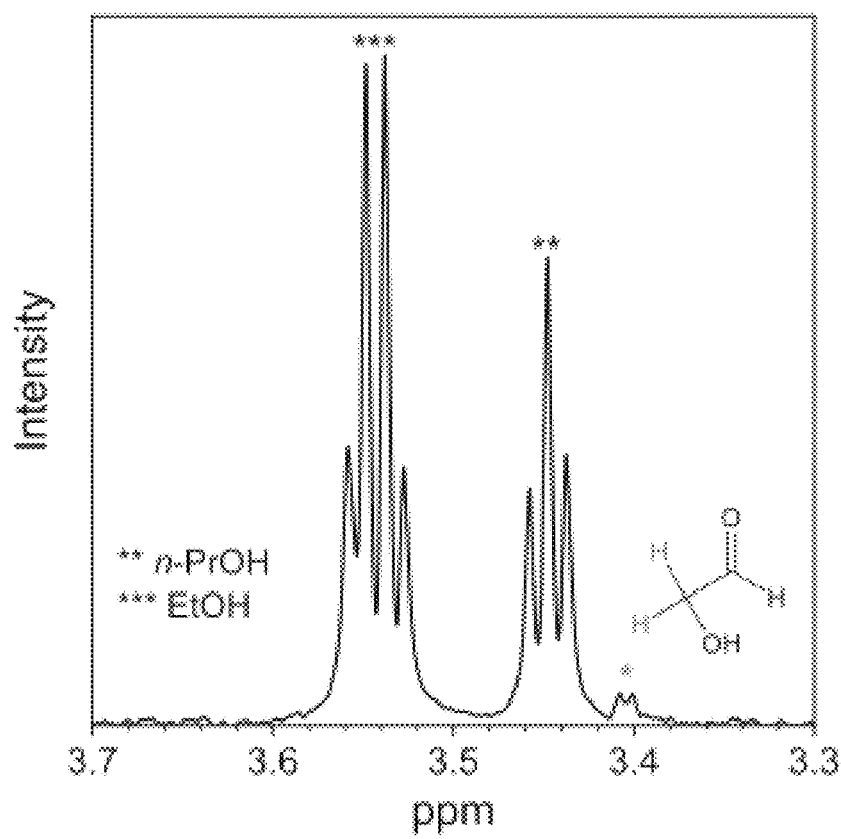
FIGS. 2A-B. Direct electrocatalytic conversion of $CO_2$ to glycolaldehyde, a "$C_2$ carbohydrate." (a) $^1$H-NMR of the product stream after 4 hours with −0.8 V vs. RHE applied bias, showing reliably detectable and quantifiable glycolaldehyde (double, 3.4 ppm) along with byproducts such as ethanol and propanol. (b) Comparison of first-hour productivity for 1 $cm^2$ cathodes including an array of state-of-the-art "oxide-derived" copper foils[10] shows that our Cu NP catalyst compares favorably for glycolaldehyde formation.
Figure 2B:
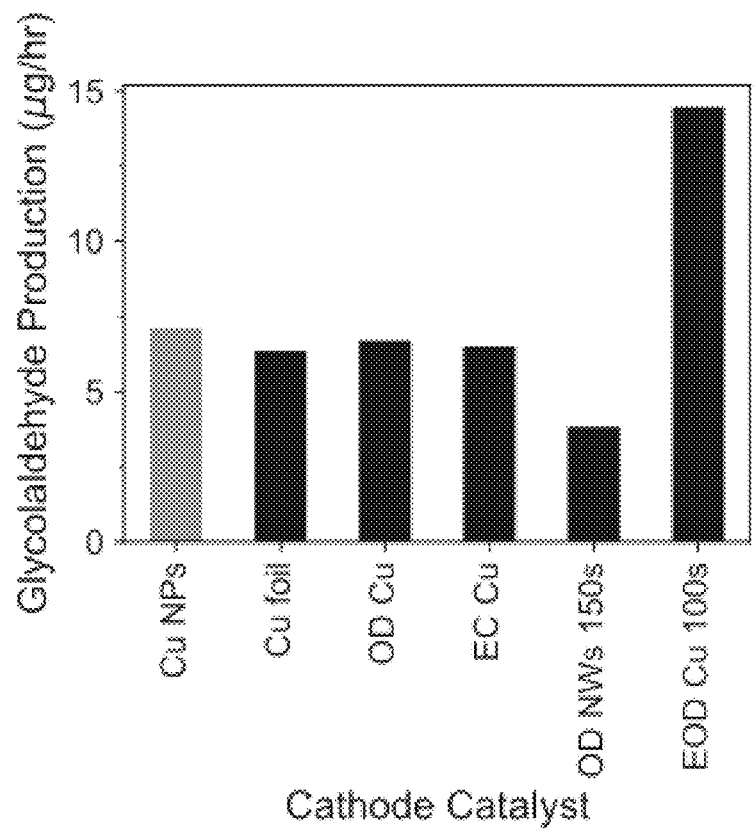

Our preliminary results show that a significant and detectable amount of glycolaldehyde can be formed from dissolved $CO_2$ in aqueous environment at applied cathodic potential ranges from −0.8 V to −1.1 V vs. RHE. FIG. 2A shows a $^1$H-NMR spectrum of the product mixture after 4 hours of electrolysis, which resulted in a product stream with 17 μM glycolaldehyde among other multi-carbon liquids such as ethanol and propanol. Notably, the average production rate of glycolaldehyde per hour over this 4-hour period is about 50% of its productivity in the first hour, suggesting some loss of selectivity for glycolaldehyde, or potentially subsequent reaction of glycolaldehyde over time. Nevertheless, we find that the first-hour productivity of this cathode compares well with other copper-based cathodes reported per $cm^2$ of cathode (FIG. 2B).[10] Glycolaldehyde is an exceedingly minor product in $CO_2$ electrocatalysis, accounting for <1% of all electrons passed in any report; however, improvements in the glycolaldehyde production rate can be obtained through catalyst optimization.

We have increased glycolaldehyde yield by increasing catalyst loading mass and total cathode surface area, as well as modification of the electrochemical cell architecture to a flow design to address the decay of productivity. Optimization can yield a further enhancement factor of ×4, sustained over 7 hours, or about 200 μg glycolaldehyde. Assuming a general sugar formula of $C_x(H_2O)_x$, the mass glycolaldehyde directly represents the mass of sugars to be made. Thus, even a formose reaction yield of 100% would only yield 200 μg sugars, which leads us to consider the formose reaction on pure $CO_2$-derived glycolaldehyde to be impractical for this purpose with present unit productivity. Hence, we adopted use of $CO_2$-derived glycolaldehyde as an autocatalyst for the formose reaction using high yields of $CO_2$-derived formaldehyde.

Figure 3:
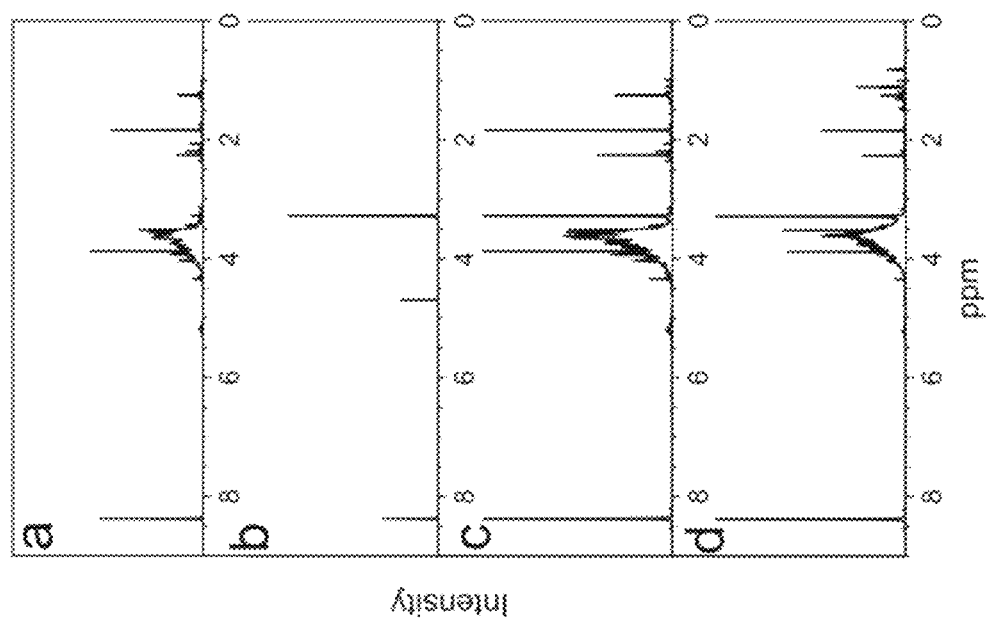
FIG. 3. Sugar generation from glycolaldehyde autocatalyzed formose reactions. (a) Model formose reaction containing 7:1 molar ratio of formaldehyde to glycolaldehyde exhibiting peaks in the 3.5-5 ppm region. (b) Glycolaldehyde-free formose reaction produces only methanol (3.31 ppm) and formate (8.51 ppm). (c) Formose reaction optimized for sugar generation with only 1 NM glycolaldehyde. (d) Formose reaction autocatalyzed with glycolaldehyde (~8 µM) from $CO_2$ electrolysis demonstrates production of sugars. All formose reactions contain $Ca(OH)_2$.

We used $^1$H-NMR with solvent suppression in order to determine the production of sugars from our reactions. Typical $^1$H-NMR chemical shifts for carbohydrate protons occur in the 3.5-5 ppm region.[11] Successful formose reactions are characterized by the appearance of multiple peaks in this region. We employed $Ca(OH)_2$, NaOH, sodium silicate and $Fe_3P$ as catalysts for model formose reactions consisting of formaldehyde and glycolaldehyde in a 7:1 molar ratio, as previously reported.[12-15] $Ca(OH)_2$ was found to be the best catalyst affording the least amount of Cannizzaro rearrangement products (formic acid and methanol), a competing reaction resulting from nucleophilic acyl substitution on an aldehyde under alkaline conditions (FIG. 3).[1] Importantly, we verified that in the absence of glycolaldehyde, pure formaldehyde under formose reaction conditions solely produces Cannizzaro rearrangement products with a clear lack of peaks in the 3.5-5 ppm $^1$H-NMR region (FIG. 3). This highlights the significance of glycolaldehyde as an autocatalyst for the generation of sugars. Next, we optimized the reaction conditions by $Ca(OH)_2$ concentration, pH, temperature, and formaldehyde concentration with the goal of minimizing the necessary glycolaldehyde to move the reaction forward in light of the glycolaldehyde concentration produced by $CO_2$ electrolysis. We were able to detect carbohydrate formation with a concentration of glycolaldehyde down to 1 μM (FIG. 3).

Subsequently, we used the $CO_2$ electrolysis product stream from the first section as the glycolaldehyde source with our optimized formose reaction conditions for the conversion of formaldehyde to sugars. The high $KHCO_3$ concentration in the electrolysis product mixture posed further obstacles. Firstly, the $Ca^{2+}$ and $CO_3^{2-}$ combine to form highly insoluble $CaCO_3$ which does not catalyze the formose reaction effectively. Secondly, $KHCO_3$ acts as a buffer which alters the optimal pH upon addition of the divalent metal catalyst. Thirdly, the high salinity of the reaction mixture could prohibit the product characterization with mass spectrometry by suppressing ionization. With further optimization we were able to sequester $CaCO_3$ and still introduce sufficient $Ca(OH)_2$ for the reaction to proceed. pH was titrated with NaOH/HCl. With these modifications, $^1$H-NMR results proved that the formose reaction can be autocatalyzed by our $CO_2$ electrolysis product containing glycolaldehyde (FIG. 3). While this example uses commercial formaldehyde to test our formose chemistry, we can also synthesize formaldehyde from $CO_2$ using industrially-established hydrogenation and formox processes, to yield sugars stemming entirely from $CO_2$ and $H_2$.

$^1$H-NMR is helpful to quickly conclude whether sugars were produced by our reactions. In addition, with $^1$H-NMR we can determine the total sugars produced by using an internal standard. The formose reaction either produces formate, methanol or sugars from formaldehyde and glycolaldehyde. Using DMSO as an internal standard we can calculate the concentration of formate and methanol with our $^1$H-NMR spectrum. Knowing the total concentration of formaldehyde (0.21 mmol in 3 mL) used in this reaction, we can then subtract the total formate and methanol from the initial formaldehyde concentration as these are also $C_1$ products to approximate the total concentration of sugars which we calculate to be 0.202 mmol in 3 mL.

Mass spectrometry (MS) remains the best technique to ascertain the identity and quantity of the sugars. Nevertheless, as was previously mentioned, the high salinity of our reaction containing $K^+$, $Na^+$ and $Ca^{2+}$ posed an obstacle. In order to separate our sugar products from the salty aqueous solution we protected their hydroxyl groups in order to increase the solubility of the sugars in an organic solvent and thus perform a liquid-liquid extraction. Using benzylation, we were able to successfully separate the sugars from the aqueous phase. The derivatization of the produced sugars by benzylation allowed their analysis by MS. Using electrospray ionization (ESI) MS, we detected a diverse mixture of fully and partially benzylated carbohydrates ranging from three to eight carbons. A couple of these sugars were found to have undergone a Cannizzaro reaction reducing their aldehyde moiety to an alcohol. As previously reported, this base mediated disproportionation likely takes place during the formose reaction which was confirmed after comparing with the ESI-MS of benzylated standards. Exact identification of all sugars produced during the formose reaction is obtained with further analytical characterization; for example, the detection of glucose for example can be done using an enzyme coupled assay with glucose oxidase.

Figure 4:
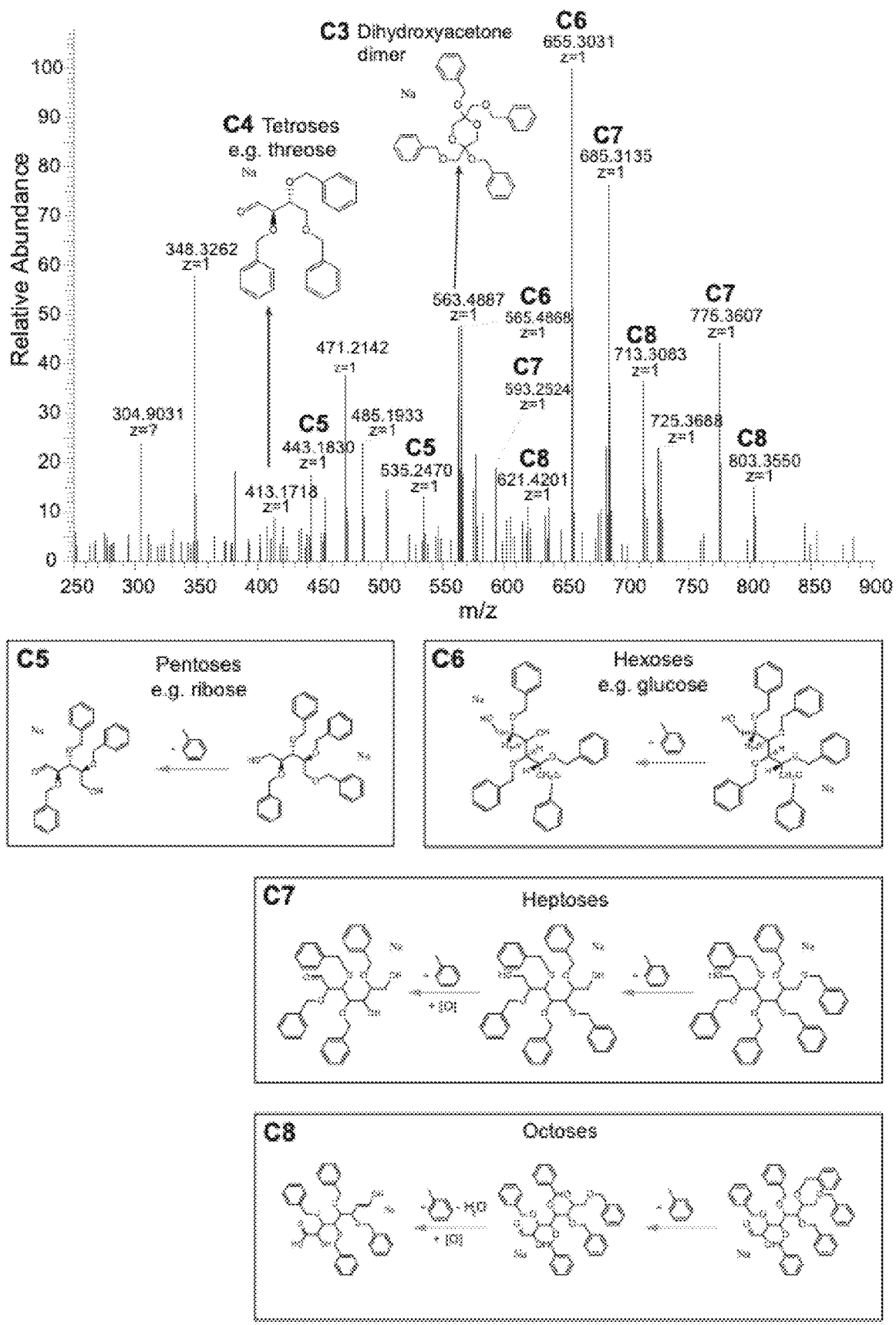
FIG. 4. Sugar synthesis catalyzed by $CO_2$ derived glycolaldehyde. (a) $^1$H-NMR spectra pre- and post-formose reaction demonstrating the appearance of carbohydrate protons in the 3.5-5 ppm region. (b) ESI-MS spectrum reveals a diverse mixture of benzylated sugars including pentoses, hexoses, heptoses, and octoses. (c) HPAEC-PAD spectrum reveals the presence of distinguishable $CO_2$ Sugars obtained from the product stream of Cu NP ensemble at −0.80 V vs RHE. Visible peaks in the chromatograms are indicated by black squares. One of them is identified as glucose as it overlays closely with the glucose reference chromatogram. Inset picture displays the product of the formose reaction without e-$CO_2$Glyc (left) and autocatalyzed by e-$CO_2$Glyc (right). The yellow color is characteristic of sugar production.

Using MS we were able to determine sugar isomers in our product mixture (FIG. 4). Overall, we produced sugars ranging from C2 to C8, including trioses, tetroses, pentoses, hexoses, heptoses, and octoses. Notably, we produced C6 sugars which may include D-glucose. With NMR we determined total sugars at 0.202 mmol in 3 mL of $H_2O$. All the sugars are dissolved in an aqueous solution at pH of 11.

Importantly, the electrochemical cell with a total capacity of 50 mL weighs 500 g, but it is typically operated with 15 mL of 0.1M $KHCO_3$ electrolyte. To produce 0.27 μmol of glycolaldehyde, our setup required 42.3 joules. The total voltage applied to the electrochemical cell during the electrochemical $CO_2$ reduction ranged from 2.3 to 2.5 V.

Figure 5:
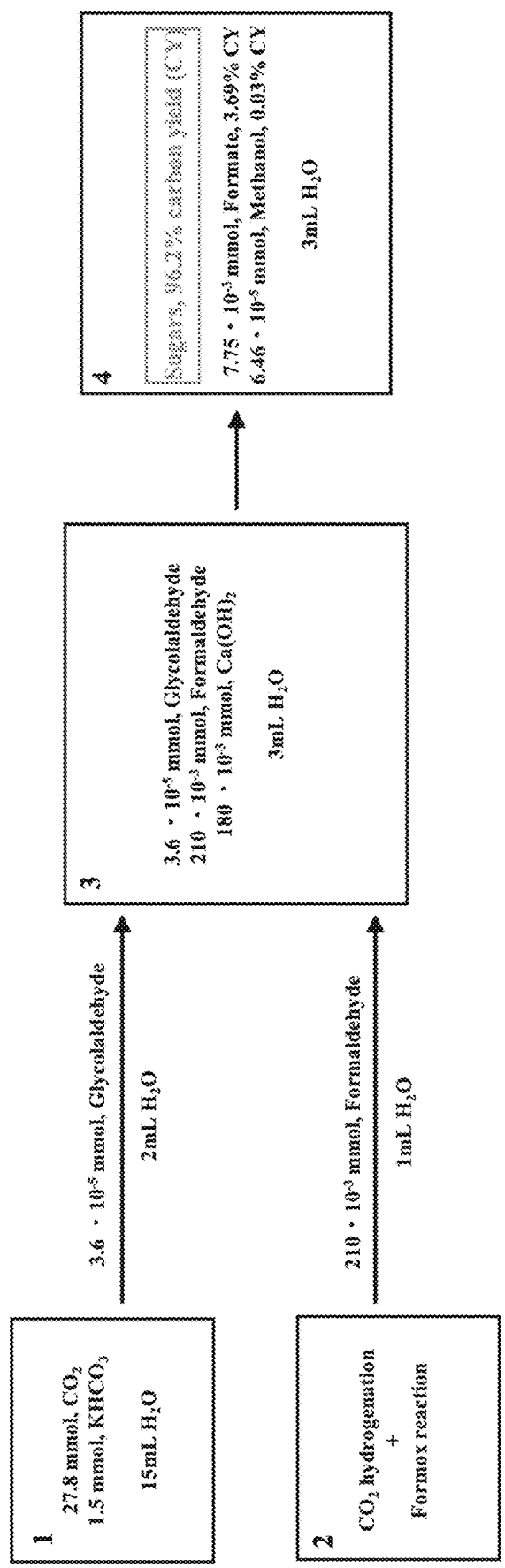
FIG. 5. Mass flow diagram. 1 Electrochemical reduction of $CO_2$ to produce autocatalyst glycolaldehyde. 2 $CO_2$ hydrogenation to methanol followed by the formox reaction converting methanol to formaldehyde. 3 Optimized formose reaction module combining glycolaldehyde and formaldehyde with divalent metal cation $Ca^{2+}$ catalyst. 4 Final product comprised of sugars with 96.2% carbon yield and minor Cannizzaro rearrangement products.

The electrochemical approach to reducing $CO_2$ has advantages including the ability to perform the reaction under mild conditions at room temperature and pressure. However, its selectivity toward specific products may be poor. Unfortunately, glycolaldehyde is a product to which $CO_2$ electrochemical reduction has very poor selectivity. It accounts for less than 1% of all electrons passed to reduce $CO_2$. In other words, the faradaic efficiency of the reaction is less than 1%. Furthermore, if carbon accounting is taken into consideration, only $2.6 \cdot 10^{-4}$% of the carbon in $CO_2$ is converted into glycolaldehyde (FIG. 5). However, our electrochemical system has $CO_2$ flowing through it, so any unreacted $CO_2$ is lost to the atmosphere. Therefore, the carbon efficiency can be improved with a $CO_2$ recycling mechanism. Furthermore, in our approach glycolaldehyde is used as an autocatalyst for the formose reaction, so its concentration requirement is very low. As we have found, the lower bound for glycolaldehyde needed to run the formose reaction is 1 μM. Therefore, for this approach it is not crucial to produce large amounts of glycolaldehyde, though it would be more energy efficient to increase its selectivity.

We provide a proof-of-concept for the conversion of $CO_2$ to formaldehyde; however, his reaction has been demonstrated at an industrial scale[6] so for expediency we used commercially available formaldehyde as a substitute to demonstrate our process. As previously explained, the glycolaldehyde from the electrochemical $CO_2$ reduction is used as an autocatalyst to convert formaldehyde into sugars. We have found that using glycolaldehyde from $CO_2$ electroreduction enables the formation of $C_{4-8}$ sugars, particularly valuable $C_6$ sugars. As per our mass flow diagram (FIG. 5), we combine glycolaldehyde and formaldehyde under optimized reaction conditions to produce sugars with roughly 96.2% carbon yield. Other minor products include formate and methanol with 3.69% and 0.03% carbon yields respectively. These minor products are a result of Cannizzaro Rearrangement during the formose reaction. Cannizzaro Rearrangement is a major obstacle to the progress of the formose reaction. Here, we have shown that using our $CO_2$ electroreduction products, we can minimize these sideproducts to less than 4% of the overall yield.

This set-up can easily scale up to produce 22.5 mL with 1.52 mmol of sugars per cycle, assuming linear scalability of the formose reaction products. The formose reaction scaling is more straightforward as it is homogeneously catalyzed as opposed to heterogeneously as is the case with $CO_2$ electroreduction. $CO_2$ electroreduction is limited by both the surface area of the cathode as well as the diffusivity of $CO_2$ in aqueous media, which is 33 mM. In order to surpass the diffusivity limit, a gas diffusion electrode can be employed. We have concurrently demonstrated that we can produce up to 100 μM of glycolaldehyde using a gas diffusion electrode system compared to 18 μM with the conventional electrode in comparable timeframes. This allows us to produce a volume of 112.5 mL of reaction product with 7.6 mmol sugars in one 5.5 hour cycle.

While the current system was optimized in a static cell setup that maintains a $CO_2$ headspace, alternative setups can account for the reduced gravity conditions using a flow-cell design instead. As previously mentioned, this optimized flow design also helps to increase the carbon efficiency by minimizing loss of unreacted $CO_2$. A flow of $CO_2$ saturated electrolyte can be maintained under these conditions by a pump using the adequate pressure.

Our system as disclosed can reliably produce sugars consistently. We show that glycolaldehyde production is dependent on copper nanocatalyst synthesis, and on the application of overpotential. Since glycolaldehyde is a minor product, it can be reduced to a negligible amount by errors in nanocatalyst synthesis or electrochemical operation. In preliminary experiments we kept the formose reaction step at a consistent temperature of 75° C. for an hour as well as pH of 11; deviations in temperature or pH produces different amounts and kinds of sugars.

Figure 6A:
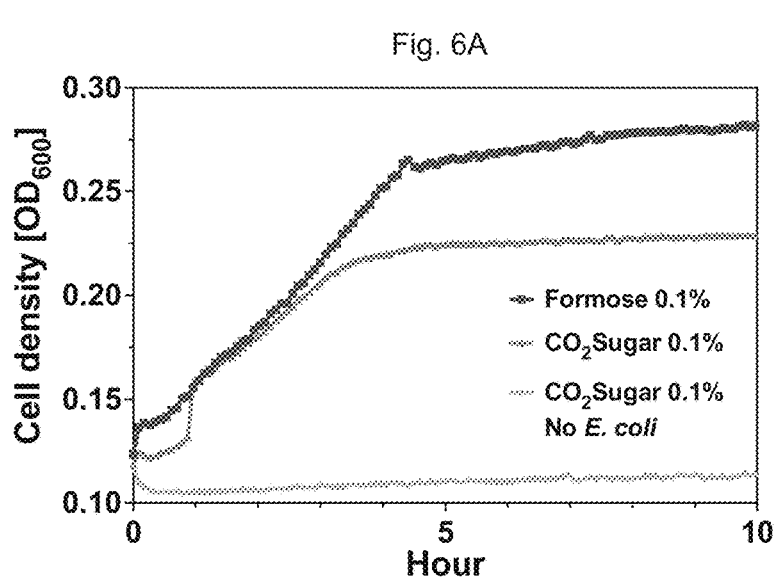
Figure 6B:
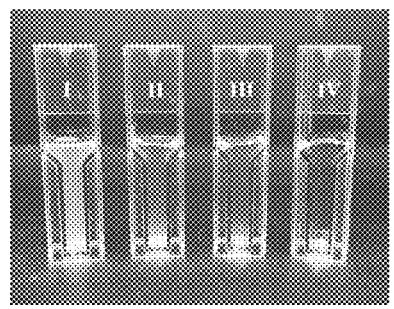
Figure 6C:
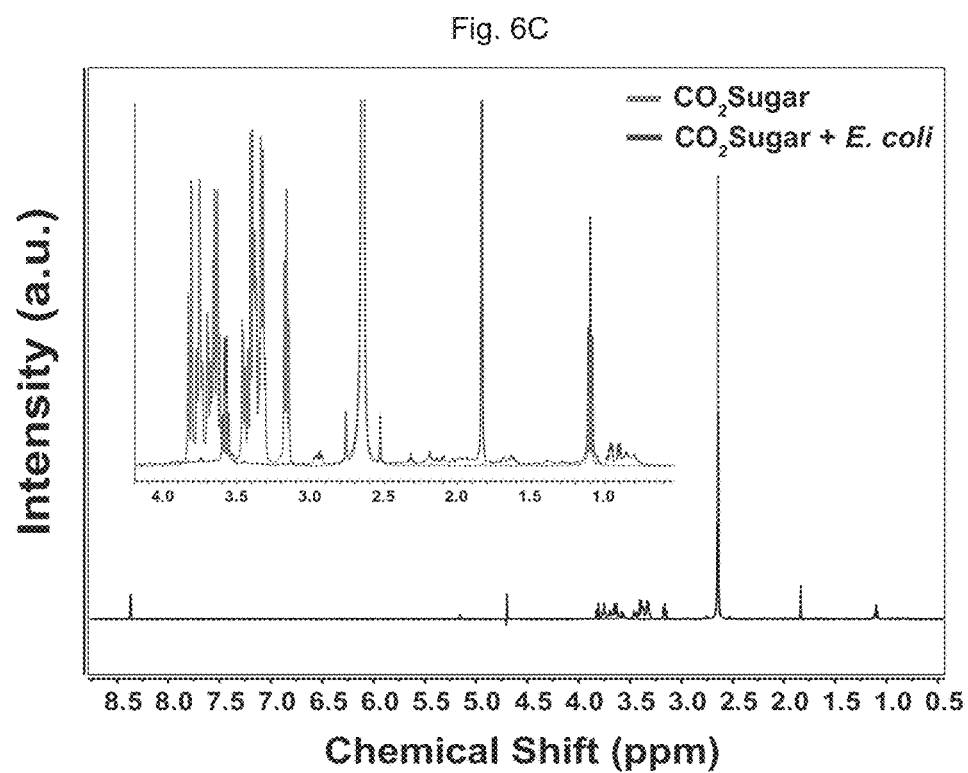

With biologically relevant sugars—ribose, galactose, fructose, arabinose, and glucose—in hand, we sought to use them to sustain bacterial growth. Glucose is the preferred source of carbon for *E. coli*; however, it can also metabolize a variety of other carbohydrates including many of those produced in the formose reaction. We collected the products from the standard formose reaction and from $CO_2$ Sugars and employed them directly as feed sources for *E. coli* cultures. We used minimal processing to prepare the formose sugars; briefly, we syringe filtered the solutions directly after the formose reaction to remove precipitates, crystallized the sugars via rotary evaporation which also removed cytotoxic components (e.g., methanol, ethanol), and added a commensurate amount (0.1% w/v) to M9 minimal bacterial medium. The medium containing the formose sugars was syringe sterilized before inoculating with *E. coli*. Culture growth and biomass accumulation were assessed by optical density. Formose- and $CO_2$ Sugars-fed cultures achieved maximum optical densities of ~0.26 and ~0.22, reaching stationary phases after 4.3 and 3.8 hours respectively (FIG. 6A). These optical density values correspond to nearly half of the maximum optical density of a control *E. coli*. culture provided with 0.1% pure glucose. The optical density of the formose-fed *E. coli* culture is expectedly lower as the feed source consists of a mixture of sugars that may not be metabolizable or metabolized suboptimally when compared to pure glucose. Nevertheless, these results demonstrate that $CO_2$ Sugars can sustain heterotrophic microorganisms in a raw form with little processing. This minimization of processing and separation steps that may be resource-prohibitive is especially valuable for industrial and extra-terrestrial applications. Furthermore, we verified that available $CO_2$ Sugars present in minimal medium were consumed during bacterial growth. To establish this, we obtained $^1$H-NMR spectra before and after the culturing period. As exhibited in FIG. 6B the carbohydrate associated proton peaks mostly disappear after bacteria are grown in the medium. Finally, *E. coli* growth can be visually confirmed in the medium containing different sugars sources (FIG. 6C). The production of $CO_2$ Sugars can be coupled with a biomanufacturing platform to generate value-added products on demand.

REFERENCES

1. Mizuno, T. & Weiss, A. H. Synthesis and utilization of formose sugars. *Adv. Carbohydr. Chem. Biochem.* 29, 173-227 (1974).
2. Breslow, R. On the mechanism of the formose reaction. *Tetrahedron Lett.* 1, 22-26 (1959).
3. Weiss, A. H., Socha, R. F., Likholobov, V. A. & Sakharov, M. M. Formose sugars from formaldehyde. *Appl. Catal.* 1, 237-246 (1981).
4. Socha, R. F., Weiss, A. H. & Sakharov, M. M. Autocatalysis in the formose reaction. *React. Kinet. Catal. Lett.* 14, 119-128 (1980).
5. Eckhardt, A. K., Linden, M. M., Wende, R. C., Bernhardt, B. & Schreiner, P. R. Gas-phase sugar formation using hydroxymethylene as the reactive formaldehyde isomer. *Nat. Chem.* (2018). doi:10.1038/s41557-018-0128-2
6. Heim, L. E., Konnerth, H. & Prechtl, M. H. G. Future perspectives for formaldehyde: Pathways for reductive synthesis and energy storage. *Green Chemistry* 19, 2347-2355 (2017).
7. Schandel, C. B., Hoj, M., Osmundsen, C. M., Jensen, A. D. & Taarning, E. Thermal Cracking of Sugars for the Production of Glycolaldehyde and Other Small Oxygenates. *ChemSusChem* 13, 688-692 (2020).
8. Ross, M. B. et al. Designing materials for electrochemical carbon dioxide recycling. *Nat. Catal.* 2, 648-658 (2019).
9. Kim, D., Kley, C. S., Li, Y. & Yang, P. Copper nanoparticle ensembles for selective electroreduction of CO2 to C2-C3 products. *Proc. Natl. Acad. Sci. U.S.A* 114, 10560-10565 (2017).
10. Lum, Y., Yue, B., Lobaccaro, P., Bell, A. T. & Ager, J. W. Optimizing C-C Coupling on Oxide-Derived Copper Catalysts for Electrochemical CO2 Reduction. *J. Phys. Chem. C* 121, 14191-14203 (2017).
11. Duus, J., Gotfredsen, C. H. & Bock, K. Carbohydrate structural determination by NMR spectroscopy: modern methods and limitations. *Chem. Rev.* 100, 4589-4614 (2000).
12. Weiss, A. H. & John, T. Homogeneously catalyzed formaldehyde condensation to carbohydrates. III. Concentration instabilities, nature of the catalyst, and mechanisms. *J. Catal.* 32, 216-229 (1974).
13. Lambert, J. B., Gurusamy-Thangavelu, S. A. & Ma, K. The silicate-mediated formose reaction: Bottom-up synthesis of sugar silicates. *Science* (80-.). 327, 984-986 (2010).
14. Pallmann, S. et al. Schreibersite: An effective catalyst in the formose reaction network. *New J. Phys.* 20, 55003 (2018).
15. Appayee, C. & Breslow, R. Deuterium studies reveal a new mechanism for the formose reaction involving hydride shifts. *J. Am. Chem. Soc.* 136, 3720-3723 (2014).

The invention claimed is:

1. A method of making a sugar, comprising the steps of electrochemical reduction of $CO_2$ to form glycolaldehyde, wherein the glycolaldehyde then operates as an autocatalyst to promote conversion of formaldehyde to the sugar in a formose reaction,
    further comprising: generating the formaldehyde from $CO_2$ through hydrogenation of CO2 to methanol, and oxidizing the methanol yields formaldehyde,
    wherein the electrochemical reduction employs:
    (i) a copper nanoparticle based electrocatalyst as a cathode in an electrochemical $CO_2$ reduction environment,
    ii) a Pt mesh as an anode to balance charge by the oxygen evolution reaction, and
    (iii) an electrochemical $CO_2$ reduction environment provided by $KHCO_3$ saturated with constantly flowing pure $CO_2$,
    wherein the formose reaction conditions include $Ca(OH)_2$, providing a divalent metal cation $Ca^{2+}$catalyst, temperature of 75° C., and pH titrated to 11;
    wherein the sugar is selected from tetroses, pentoses, hexoses, heptoses and octoses.
2. The method of claim 1, powered by solar energy and performed in an extraterrestrial environment.
3. The method of claim 1, further comprising isolating the resultant sugar.
4. The method of claim 1, further comprising formulating the resultant sugar in a feedstock configured for *E. coli* bacteria.
5. The method of claim 1, wherein sugar production is over 96% of carbon yield, and side-product production, including formate and methanol, is less than 4%.

* * * * *